United States Patent
Shioi et al.

(10) Patent No.: US 7,391,516 B2
(45) Date of Patent: Jun. 24, 2008

(54) OPTICAL ELEMENT FOR MEASURING INFORMATION OF LIVING BODY AND DEVICE FOR MEASURING INFORMATION OF LIVING BODY USING THE OPTICAL ELEMENT

(75) Inventors: Masahiko Shioi, Katano (JP); Shinji Uchida, Neyagawa (JP); Kiyoko Oshima, Shijonawate (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 320 days.

(21) Appl. No.: 10/547,670

(22) PCT Filed: Mar. 28, 2005

(86) PCT No.: PCT/JP2005/005708

§ 371 (c)(1),
(2), (4) Date: Sep. 2, 2005

(87) PCT Pub. No.: WO2005/092192

PCT Pub. Date: Oct. 6, 2005

(65) Prior Publication Data
US 2006/0183982 A1    Aug. 17, 2006

(30) Foreign Application Priority Data
Mar. 29, 2004    (JP)    .............................. 2004-096242

(51) Int. Cl.
G01N 21/00    (2006.01)
G01N 33/48    (2006.01)
(52) U.S. Cl. .......................................... 356/432; 356/39
(58) Field of Classification Search ................. 600/310, 600/323; 356/39–42, 439
See application file for complete search history.

(56) References Cited

U.S. PATENT DOCUMENTS

| 5,313,940 A | * | 5/1994 | Fuse et al. | 600/310 |
| 5,385,143 A | * | 1/1995 | Aoyagi | 600/310 |
| 6,150,665 A | * | 11/2000 | Suga | 250/556 |
| 6,223,063 B1 | * | 4/2001 | Chaiken et al. | 600/310 |
| 6,505,061 B2 | * | 1/2003 | Larson | 600/323 |

(Continued)

FOREIGN PATENT DOCUMENTS

JP    09-113439    5/1997

(Continued)

*Primary Examiner*—L. G. Lauchman
*Assistant Examiner*—Jarreas C Underwood
(74) *Attorney, Agent, or Firm*—McDermott Will & Emery LLP (57) ABSTRACT

The present invention provides an optical element for measuring information of living body for noninvasively measuring a body fluid component in a test sample of living body with high accuracy, stability, and ease. The optical element includes a light incident surface, a contact surface contacting living body and having a groove to protrude living body and a light emission surface, in which a light incident from the light incident surface is applied to living body, and the light absorbed and scattered by living body is received and emitted from the light emission surface, a light transmittance controlling means is formed from the bottom part of the valley part of the groove, on at least a part of a wall surface of the light incident surface side and/or on a wall surface of the light emission surface side of the groove.

9 Claims, 4 Drawing Sheets

U.S. PATENT DOCUMENTS

| | | | |
|---|---|---|---|
| 6,580,086 B1 * | 6/2003 | Schulz et al. | 250/557 |
| 6,687,521 B2 * | 2/2004 | Sato et al. | 600/344 |
| 6,882,872 B2 * | 4/2005 | Uchida et al. | 600/310 |
| 6,993,160 B2 * | 1/2006 | Miura et al. | 382/115 |
| 7,167,735 B2 * | 1/2007 | Uchida et al. | 600/310 |
| 2002/0038078 A1 * | 3/2002 | Ito | 600/309 |
| 2003/0109030 A1 * | 6/2003 | Uchida et al. | 435/287.1 |

FOREIGN PATENT DOCUMENTS

| | | |
|---|---|---|
| JP | 11-155844 | 6/1999 |
| JP | 11-178799 | 7/1999 |

* cited by examiner

OPTICAL ELEMENT FOR MEASURING INFORMATION OF LIVING BODY AND DEVICE FOR MEASURING INFORMATION OF LIVING BODY USING THE OPTICAL ELEMENT

This application is the U.S. National Phase under 35 U.S.C. § 371 of International Application No. PCT/JP05/005708, filed Mar. 28, 2005, which in turn claims the benefit of Japanese Application No. 2004-096242, filed Mar. 29, 2004, the disclosures of which Applications are incorporated by reference herein in their entirety.

TECHNICAL FIELD

The present invention relates to an optical element used for optically measuring tissue of a living body to noninvasively measure a living body component such as glucose, cholesterol, urea, or triglyceride in a body fluid, and to an apparatus for measuring information of a living body using the optical element.

BACKGROUND ART

Conventionally, there have been proposed various methods in which a specific component in a living body or in a solution are measured by using an optical measuring device. For example, there has been known a method in which a blood-sugar level is measured by bringing upper and lower lips into intimate contact with a transparent attenuated total reflectance (ATR) element having a pair of reflecting surfaces facing in parallel.

In this method, an ATR element which is an ATR prism comprising zinc selenide, silicon, or germanium is held in a mouth, and a light is applied to the ATR element while the ATR element is pressed by the lips, and an analysis is conducted for a light emitted to the outside of the ATR element after total reflections are repeated between the reflecting surfaces of the ATR element and the lips.

In the above method, evanescent wave (so-called penetrating light) is applied to a quantitative analysis. A light traveling in the ATR prism is reflected, after slightly going into lips. Therefore, the light is affected by each component in a body fluid existing in the lips.

For this reason, variations in reflectance and absorptance of a body fluid can be detected by measuring the amount of the reflected light, thereby enabling to obtain information about each component in the body fluid.

In Japanese Laid-Open Patent Publication No. Hei 11-178799, for example, there has been disclosed a method in which properties and characteristics of surface layer tissues, preferably skin tissues or mucous membrane tissues, further preferably dermis tissues or subcutaneous tissues in the skin tissues, or lamina propria mucosae or submucosal layer in mucous membrane tissues of a living body are analyzed by light absorption.

In this method, a part of surface layer tissues of a living body is protruded by using a groove, and a spectrum analysis is conducted by light receiving and applying operations from a light emission part and to a light incident part facing each other interposing the protruded part in between.

Based on this method, sufficient signals for the measurement can be obtained, and information of the living body components can be obtained even with a usage of near-infrared light of 1.4 to 2.5 micrometers, which is absorbed by living body in a greater degree. Additionally, an optical path length of the light transmitting the living body can be determined from the size of the groove. It is known from the Lambert-Beer Law that a light absorption amount of a living body is proportional to the optical path length.

Thus, the fact that the optical path length can be automatically determined from the size of the groove has quite significant meaning in measurements using light, and is a great advantage in this method.

Also, International Publication No. WO 01-58555 recites a contact element (optical measurement device) for measuring information of living body comprising an abutting means having a recess for abutting the living body, a detecting light emission means which emits the detecting light from a part in the recess, and a detecting light incident means provided in other part in the recess for applying the detecting light, characterized in that the detecting light is applied to the detecting light incident means after passing through the living body tissue inserted in the recess, while the abutting means abutting the living body tissues. The contact element is proposed by an intention to improve the contact between a surface of the living body and an optical censor for improving measurement accuracy.

DISCLOSURE OF INVENTION

However, the conventional optical measurement method and optical measurement device such as the above had the following problems. First, in the conventional method using the ATR element, it is known that a penetration depth "d" of the evanescent wave into a living body can be obtained approximately by the numerical formula (1):

$$d = \frac{\lambda_0}{2\pi(n_1^2\sin^2\theta_1 - n_2^2)^{\frac{1}{2}}}$$

$d$: penetration depth $\lambda_0$: wave length in a vacuum $n_1$: index of reflection in a first medium $n_2$: index of reflection in a second medium $\theta_1$: incident angle from the first medium to the second medium In the numeral formula (1), $\lambda$ is wave length of a light, $\theta$ is incident angle, $n_1$ is an index of reflection of a crystal, and $n_2$ is an index of reflection in the medium contacting the crystal.

Herein, as an example, a penetration depth "d" is calculated for the case when the wave length of the light was set to become 10 μm, ZnSe crystal (approximate index of reflection 2.0) as an ATR prism is used, incident angle is set to become 45 degree, and water (approximate index of reflection 1.3) is used as the surrounding medium: and d=5.7 μm is obtained from the numeral formula (1). In the calculation conducted for a living body, the index of reflection of the living body is about 1.3 to 1.5, and d=29 μm is obtained when $n_2$=1.41. It is revealed that information on condition of several tens of micron from surface and its proximity can be obtained.

Additionally, it is known that an electric field of the evanescent wave is attenuated according to the reaching depth of the evanescent wave exponentially. Therefore, the signals to be obtained are attributed mostly to horny layer and saliva which are at a shallow depth. Since there is no information on living body in horny layer and in saliva, it can be thought that these signals contain very little information of living body.

Moreover, it can be thought that the thicknesses of saliva and horny layer change in every measurement. By the thickness variation in the saliva and horny layer, optical path length of a light passing through the tissue of living body changes. By the changes in the optical path length of a light passing through the tissue of living body, the amount of light absorption by tissue of living body changes at every measurement due to causes other than the information of the living body. From the above two points, it is thought that measurement with a method using the ATR element is very difficult.

Also, in the method of Japanese Laid-Open Patent Publication No. Hei 11-178799, the tissue of living body is protruded by bringing the tissue of living body into contact with the groove and recess formed, and then a light is introduced into the tissue of living body by using an optical fiber. By using the optical fiber, target part of the living body can be selectively measured.

On the other hand, the usage of the optical fiber makes an assembly very difficult, and few optical fiber materials can be used when mid-infrared light of 10 µm band is to be used. For such materials, silver chloride/silver bromide fiber, KRS-5 fiber, and hollow optical fiber may be mentioned, for example.

The silver chloride/silver bromide fiber has poor resistance to moisture, and when used in the air, moisture in the air is absorbed and the fiber becomes unusable. The KRS-5 fiber is extremely poisonous, and preferably used without any contact with a living body.

Also, although the hollow optical fiber is able to guide mid-infrared light efficiently, thin films necessary to guide the mid-infrared light have to be formed in the hollow part. Therefore, making the fiber ultra fine is very difficult.

Also, in the methods of Japanese Laid-Open Patent Publication No. Hei 11-178799 and International Publication No. WO 01-58555, the bottom of a valley part of the above groove and recess will become very small in size, thereby making it impossible for the tissue of living body to go into the above valley part. Therefore, the degree of contact of the tissue of living body onto the bottom part of the valley of the groove and the recess will decline.

On the other hand, at the peak part of the groove and the recess respectively, the tissue of living body is deformed greatly, and the tissue of living body can not precisely follow the forms of the groove and the recess for the deformation. Therefore, the degree of contact will decline also at the peak parts of the groove and the recess.

Herein, viewing the optical element from the side, the peak part of the groove and the recess refers to the edge (rib) between the grooves and between the recesses where the tissue of living body makes contact with the groove and the recess for the first time: and the valley part refers to the most far part corresponding to the part in the groove and the recess far from the tissue of living body.

Additionally, the decline in degree of contact results in a condition which causes adverse effects to the measurement due to interventions of the material other than the tissue of living body, such as air, saliva, sweat, tears, or the like, which will cause reflection and scattering of the light between the tissue of living body and the intervening material and also the change in the optical path length of the light passed through the tissue of living body. Thus, the degree of contact greatly affects the light absorptions of the tissue of living body, and the decline in the degree of contact will increase errors. Therefore, the measurement in the conventional methods such as the above is very difficult.

In light of the above circumstances, the present invention aims to provide an optical element for measuring information of living body and a device for measuring information of living body using the optical element, which can noninvasively measure a body fluid component in test sample such as a living body with high accuracy, stability and ease.

MEANS FOR SOLVING THE PROBLEM

In order to solve the above problem, the present invention provides an optical element for optically measuring information of living body, comprising: a light incident surface, a contact surface contacting the living body and having a groove to protrude the living body, and a light emission surface, for applying a light incident from the light incident surface to the living body, receiving a light absorbed and scattered by the living body, and emitting the received light to the outside from the light emission surface, wherein a light transmittance controlling means is provided at the groove, and the light transmittance controlling means is formed, from the bottom part of a valley part of the groove, on at least a part of a wall surface of the light incident surface side and/or the light emission surface side of the groove.

The light transmittance controlling means can be further provided at a part except for the groove, the light incident surface, and the light emission surface. Also, it is preferable that the light transmittance controlling means is provided at least at a peak part of the groove.

The peak part of the groove refers to the edge (rib) between the grooves where the living body makes contact with the groove for the first time: and the valley part refers to the most far part corresponding to the part in the groove far from the living body.

The light transmittance controlling means can be made of light absorbing material, light scattering material, or light reflecting material, and can be composed from any of single-layered film and multiple-layered film.

Further, the present invention also relates to an apparatus for measuring information of living body, comprising: a light source, the above optical element, a photodetector for detecting a light emitted from the optical element, and a processor for processing information obtained from the photodetector.

EFFECTS OF THE INVENTION

Based on the above structure, even though the degree of the contact between the tissue of living body and the above groove is declined when the bottom of the valley part of the groove became small in size to prevent the tissue of living body to go into the above valley part, and when the tissue of living body is deformed at the peak part in between the grooves, a light can be applied only to a part where the degree of the contact is high, and the light from the part with high degree of contact can be securely emitted. Therefore, by using the optical element of the present invention, a body fluid component in a test sample such as a living body can be measured noninvasively with high precision, stability, and ease.

Thus, according to the present invention, in an apparatus for measuring information of living body including an optical element having a groove, the effects of the insufficiency in the degree of contact can be alleviated and a concentration of a target component in a test sample can be measured with stability and ease.

BEST MODE FOR CARRYING OUT THE INVENTION

In the following, embodiments of an optical element for measuring information of living body of the present invention having a light incident surface, a contact surface having a groove to contact a tissue of living body and protrude the living body, and a light emission surface, the groove further comprising a light transmittance controlling means, will be described in detail, referring to the drawings. In the following description, the same reference numerals are used for the same or corresponding parts, and repetitive description may be omitted. Also, the following embodiments are an example of the present invention and are not intended to be limiting.

EMBODIMENT 1

Figure 1:
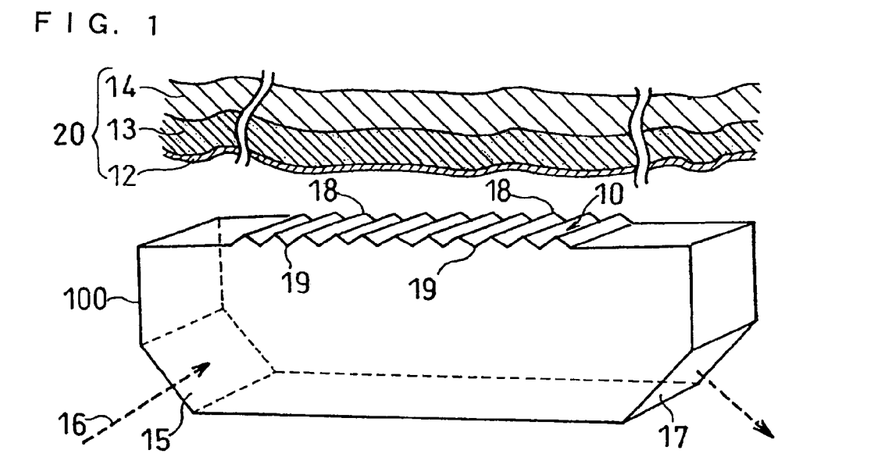
FIG. 1 is a perspective view illustrating an optical element for measuring information of living body in an embodiment of the present invention.
Figure 2:
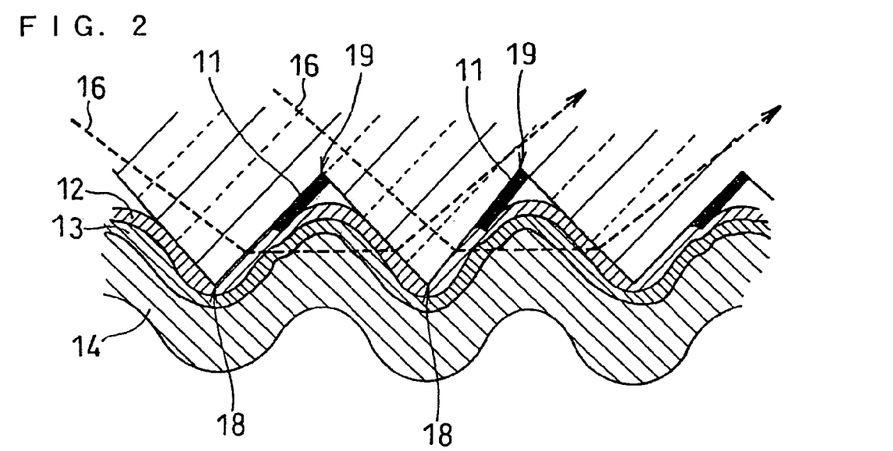
FIG. 2 is a cross sectional, enlarged, upside-down view of a part where the groove 10 and the tissue of living body 20 in FIG. 1 are making contact.

FIG. 1 is a perspective view illustrating an optical element for measuring information of living body in an embodiment of the present invention. Also, FIG. 2 is a cross sectional, enlarged, upside-down view of a part where the groove 10 and the living body 20 are making contact. As shown in FIG. 1, an optical element 100 for measuring information of living body of this embodiment has a groove 10.

In the groove 10, a part where the living body 20 makes the first contact is a peak part 18, and the bottom of the groove 10 is a valley part 19, viewing the optical element 100 for measuring information of living body from the side.

In this embodiment, wavelength of the light to be measured is to be a light in the range of mid-infrared light not less than 2.5 μm. A light 16 is applied from a light incident surface 15. The light 16 applied is emitted from the optical element 100 for measuring information of living body once at the groove 10, as shown in FIG. 2.

The light 16 emitted is refracted at the living body 20 contacting the groove 10, passed through the living body 20, refracted again at an interface between the living body 20 and the groove 10, and applied into the optical element 100 for measuring information of living body.

The light 16 applied into the optical element 100 for measuring information of living body is emitted from a light emission surface 17. Herein, in this embodiment, the tissue of living body 20 is a skin, and a horny layer 12 exists at the outermost surface of the skin. Also, below the horny layer 12, a granular layer (not shown) of approximately one or two layers of cell exists, and below the granular layer, a prickle layer 13 exists. And below the prickle layer, a basal layer (not shown) and dermis 14 exist.

In measuring information of living body, the horny layer 12 is so-called "dead cell," and is an obstructive factor in the measurement. Therefore, it is preferable that the horny layer 12 is not to be measured. It is preferable that the prickle layer 13 and the dermis 14 are measured, considering that the cells are engaged in living activities.

Next, a behavior of a light at an interface between the groove 10 and the tissue of living body 20 will be described in detail, referring to FIG. 2. When the tissue of living body 20 is made to have contact with the groove 10, as shown in FIG. 2, the horny layer 12, the prickle layer 12, and the dermis 14 go into the groove 10. Among these, since the horny layer 12 is so-called "dead cell" as mentioned above, it works as an obstructive layer when measuring a body fluid component of a living body.

Also, as mentioned above, the bottom part of the valley part 19 of the groove 10 becomes very small in size, and the tissue of living body 20 does not go into the groove 10 completely, thereby making the degree of contact worse. Further, at the peak part 18, although the tissues of living body 20 are deformed greatly as well by the groove 10, the tissue of living body can not follow the form of the groove precisely, thereby making the degree of contact worse.

Therefore, in the optical element for measuring information of living body of the present invention, a light transmittance controlling means 11 is provided to cover the part where the degree of the contact is insufficient.

Herein, the region to provide the light transmittance controlling means 11 is to be explained. When the measurement wavelength is in mid-infrared range, the distance that the light can be transmitted in a living body is approximately 100 μm. Therefore, it is preferable that the width of an opening of the groove 10 is set to become about 100 μm. At this time, with regard to the valley part 19 of the groove 10, it is preferable that at least 10 μm of the light transmittance controlling means 11 is formed, from the bottom part of the valley part 19 of the groove 10, along the wall surface on the side of the light incident surface of each groove 10, considering the thickness of the horny layer 12, as shown in FIG. 2.

Figure 3:
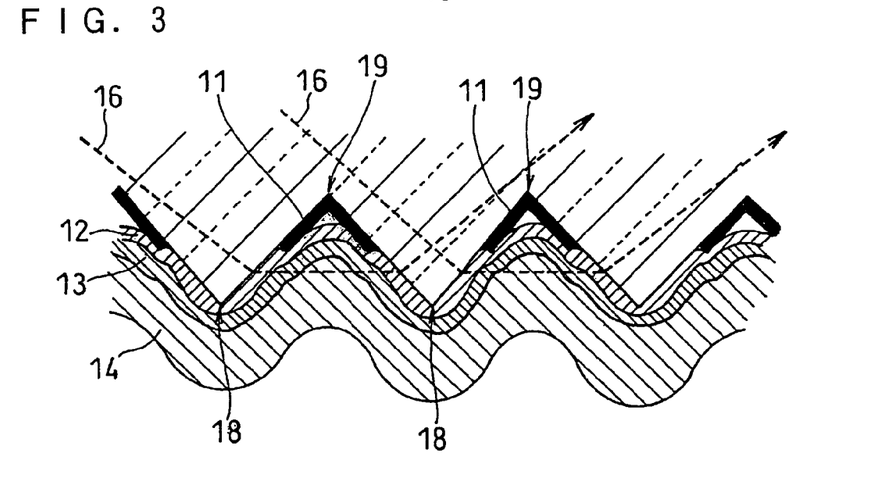
FIG. 3 is another cross sectional, enlarged, upside-down view of a part where the groove 10 and the tissue of living body 20 in FIG. 1 are making contact.

Also, as shown in FIG. 3, it is also preferable that in addition to the wall surface of the side of light incident surface of each groove 10, at least 10 μm of the light transmittance controlling means 11 is formed from the bottom part of the valley part 19 of each groove 10, along the wall surface on the side of the light emission surface of each groove 10.

Further, in view of decreasing the part of insufficient degree of contact as much as possible, it is preferable that the light transmittance controlling means 11 of not less than 30 μm is formed.

Figure 4:
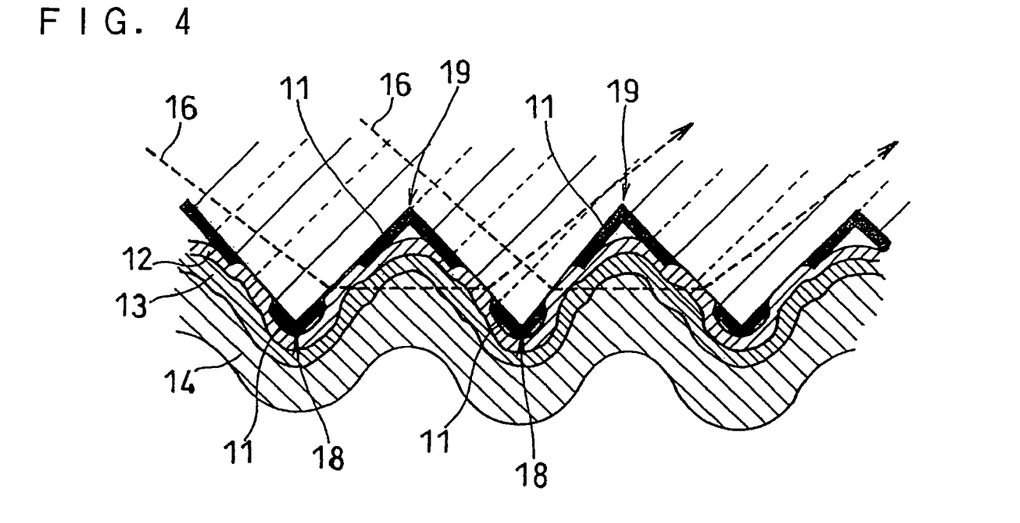
FIG. 4 is still another cross sectional, enlarged, upside-down view of a part where the groove 10 and the tissue of living body 20 in FIG. 1 are making contact.

Additionally, it is also preferable that the light transmittance controlling means 11 is provided at a peak part 18 of the groove 10. In such case, it is preferable to provide at least 5 μm of it from the edge of the peak part 18, along the wall surface of the groove 10, as shown in FIG. 4. In the peak part 18, the light transmittance controlling means 11 can be provided at one of or at both of the wall surface of the light incident surface side and wall surface of the light emission surface side.

By providing the light transmittance controlling means 11, the light 16 passes through the part where the light transmittance controlling means 11 is not provided. Based on this, the prickle layer 13 which includes information of living body, and further the dermis 14 which includes more information of living body than the prickle layer 13 can be measured mainly. And by becoming able to decrease the light 16 that passes through the region where the degree of contact is insufficient by the light transmittance controlling means 11, stable and easy measurement of information of living body can be made possible.

Herein, the light transmittance controlling means 11 of the present invention restrains an optical path from the optical element to the tissue of living body, for example, to not transmit the light to the part where only the horny layer exists and the degree of contact between the tissue of living body and the optical element is insufficient, and the part where the measurement is not suitable, by absorbing, reflecting, scattering, interfering, and/or diffracting the light. Therefore, the light transmittance controlling means 11 may be a means to completely shield the light, and may be a means to attenuate the light.

For example, for the light 16, an infrared light of approximately 10 μm can be used, and for the light transmittance controlling means 11, $SiO_2$ and the like of a light absorbing material can be used.

EMBODIMENT 2

The wavelength of the light for the measurement in this embodiment is to be a light in near-infrared range below 2.5 μm. In this embodiment, the size of groove 10 and the length of the light transmittance controlling means 11 (that is, the length of the part where a light transmittance controlling means 11 is formed) are different, compared with the Embodiment 1.

When the measurement wavelength is in the near-infrared range, the distance which the light can pass through in the living body is approximately 2 mm. Therefore, it is preferable that the width of an opening of the groove 10 is set to become approximately 2 mm. At this time, in a valley part 19 of the groove 10, it is preferable that a light transmittance controlling means 11 of at least 100 μm is formed from the bottom part of the valley part 19 of the groove 10, along the wall surface of a light incident surface side of each groove 10, as shown in FIG. 2.

Also, it is preferable that the light transmittance controlling means 11 of at least 100 μm, is formed in addition to the wall surface of the light incident surface side of each groove 10, from the bottom part of the valley part 19 along the side wall of the light emission surface side of each groove 10, as shown in FIG. 3.

Further, in view of decreasing the part where the degree of contact is insufficient as much as possible, it is preferable that the light transmittance controlling means 11 of not less than 300 μm is formed.

Additionally, it is preferable that the light transmittance controlling means 11 is provided at the peak part 18 of the groove 10. In such case, it is preferable to provide it of at least 50 μm from the edge of the peak part 18 along the wall surface of the groove 10, as shown in FIG. 4. In this peak part 18, the light transmittance controlling means 11 can be provided at either one of or both of the wall surface of the light incident surface side and the wall surface of the light emission surface side.

By providing the light transmittance controlling means 11 in such manner, the light 16 is transmitted where the light transmittance controlling means 11 is not provided. Based on this, the prickle layer 13 including the information of living body, and further the dermis 14 including more information of living body than the prickle layer 13 can be measured mainly. And additionally, since the light 15 being transmitted to the region where the degree of contact is insufficient can be decreased by the light transmittance controlling means 11, the information of living body can be measured stably and easily.

Herein, the light transmittance controlling means 11 of the present invention restrains an optical path from the optical element to the tissue of living body, for example, to not transmit the light to the part where only the horny layer exists and the degree of contact between the tissue of living body and the optical element is insufficient, and the part where the measurement is not suitable, by absorbing, reflecting, scattering, interfering, and/or diffracting the light.

Therefore, the light transmittance controlling means 11 may be a means to completely shield the light, and may be a means to attenuate the light.

EMBODIMENT 3

Figure 5:
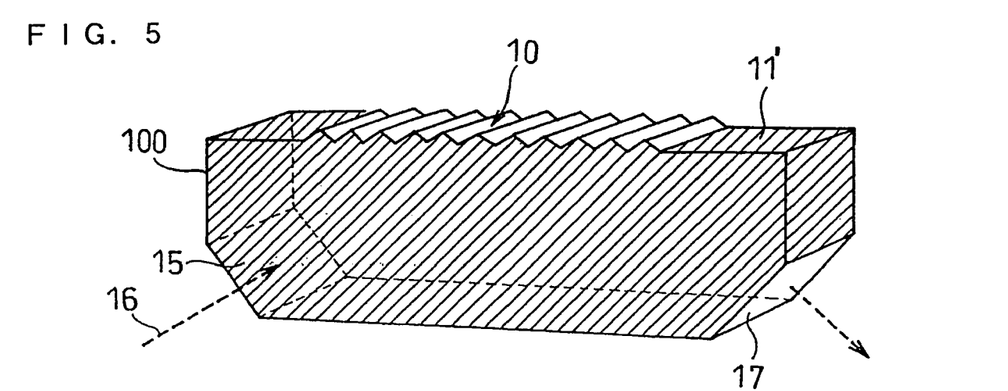
FIG. 5 is a perspective view illustrating a structure of an optical element for measuring information of living body in another embodiment of the present invention.

FIG. 5 is a perspective view illustrating a structure of an optical element for measuring information of living body in another embodiment of the present invention. An optical element 100 for measuring information of living body shown in FIG. 5 has a light transmittance controlling means 11' on a part except for a groove 10, a light incident surface 15, and a light emission surface 17. That is, as shown with the hatch pattern portions in FIG. 5, the light transmittance controlling means 11' is provided at an entire surface of the optical element 100 for measuring information of living body except for the groove 10, the light incident surface 15 and the light emission surface 17.

In the groove 10, the light transmittance controlling means 11 is provided as in any of the case shown in FIGS. 2 to 4.

Figure 6:
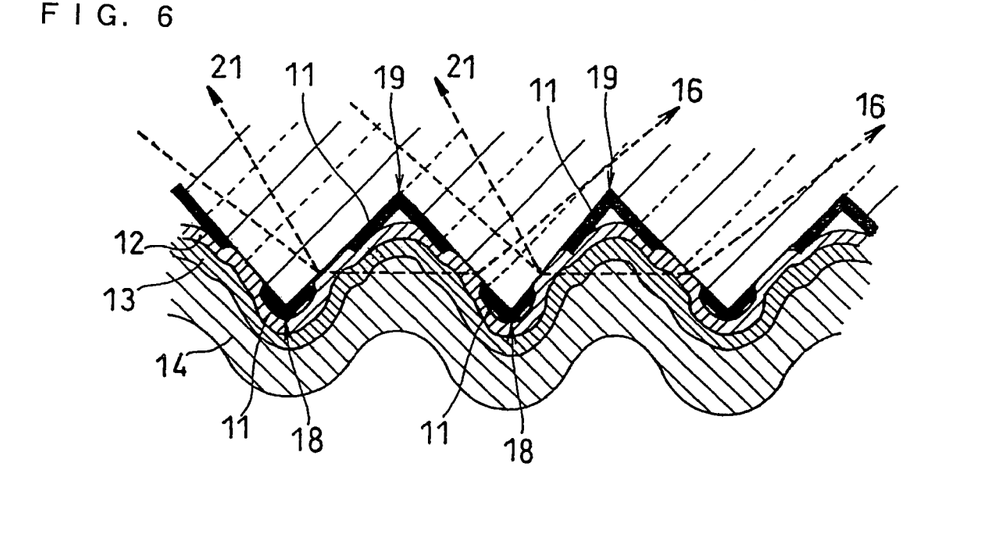
FIG. 6 is still another cross sectional, enlarged, upside-down view of a part where the groove 10 and the tissue of living body 20 are making contact.

When the light 16 is entered in the groove 10, there exist a transmitted light which is emitted from the groove 10 and from the optical element 100 for measuring information of living body to the outside, and a reflected light 21 which returns into the optical element 100 for measuring information of living body again (ref. FIG. 6). The reflected light 21 repeats reflections at various surfaces inside the optical element 100 for measuring information of living body.

Among the reflected light 21, there exists a light which is entered into the tissue of living body 20 again and emitted from the light emission surface 17. An error may be caused when this reflected light 21 is absorbed by the tissue of living body 20 and the absorbed light is detected.

Therefore, as shown in FIG. 5, the reflected light 21 which is reflected by the interface between the groove 10 and the horny layer 12 is attenuated by the light transmittance controlling means 11' provided on a surface except for the light incident surface 15, the light emission surface 17, and the groove 10.

Based on this, error factors based on the reflected light 21 can be reduced, in addition to the error factors based on the insufficient degree of contact, and on the light that transmitted only to the horny layer 12, as noted above.

EMBODIMENT 4

Figure 7:
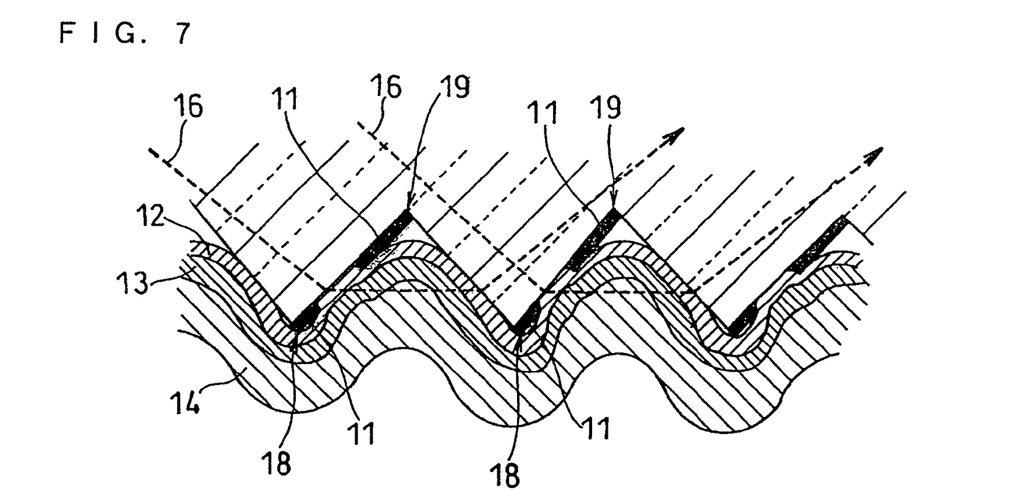
FIG. 7 is a cross sectional, enlarged, upside-down view of a part where the groove 10 of an optical element for measuring information of living body and the tissue of living body 20 are making contact in still another embodiment of the present invention.

Next, FIG. 7 is a cross sectional, enlarged, upside-down view of a part where a groove 10 of an optical element for measuring information of living body and a tissue of living body 20 are making contact in still another embodiment of the present invention. An optical element 100 for measuring information of living body shown in FIG. 7 has a light transmittance controlling means 11 only on a wall surface of a light incident surface side of the groove 10.

In this case, when the light transmittance controlling means 11 is made of a light reflecting material, even though the light transmittance controlling means 11 is provided only on the wall surface of the light incident surface side, a light can be reflected with the reflectance of nearly 100%.

In this case, it is preferable that the light transmittance controlling means 11' is provided on the entire surface except for the light incident surface 15, the light emission surface 17, and the groove 10, as in the case of the Embodiment 2 above. This is because the light reflected by the light transmittance controlling means 11 is removed by the light transmittance controlling means 11' provided on the surface except for the groove 10, the light incident surface 15, and the light emission surface 17 to not affect the measurement.

Also, even though the material other than the light reflecting material is used for the light transmittance controlling means 11 to be provided in the groove 10, when performance of the light transmittance controlling means 11 is satisfactory, the light transmittance controlling means 11 can be provided only on one wall surface of the groove 10.

Figure 8:
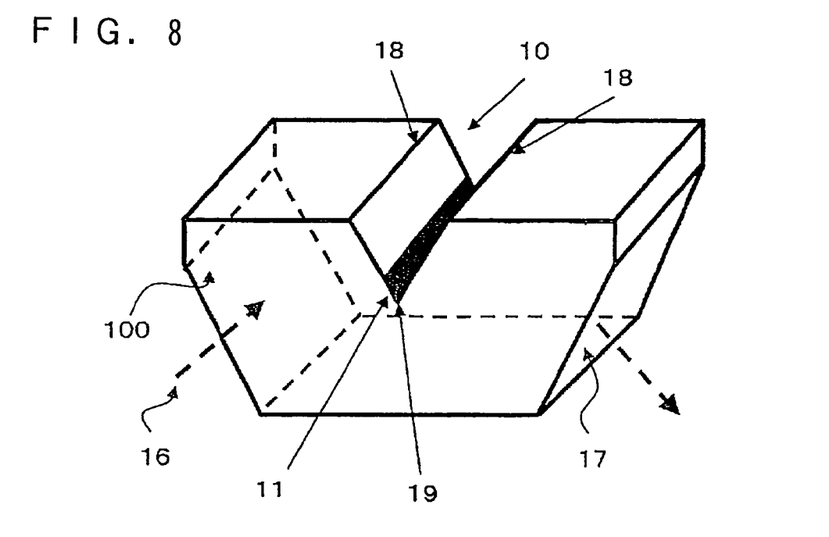
FIG. 8 is a perspective view of a structure of an optical element for measuring information of living body in still another embodiment of the present invention.

Although in the Embodiments 1 to 4, there are described the cases when a plurality of the grooves 10 are provided, the groove 10 can be in the singular, as shown in FIG. 8.

EMBODIMENT 5

Figure 9:
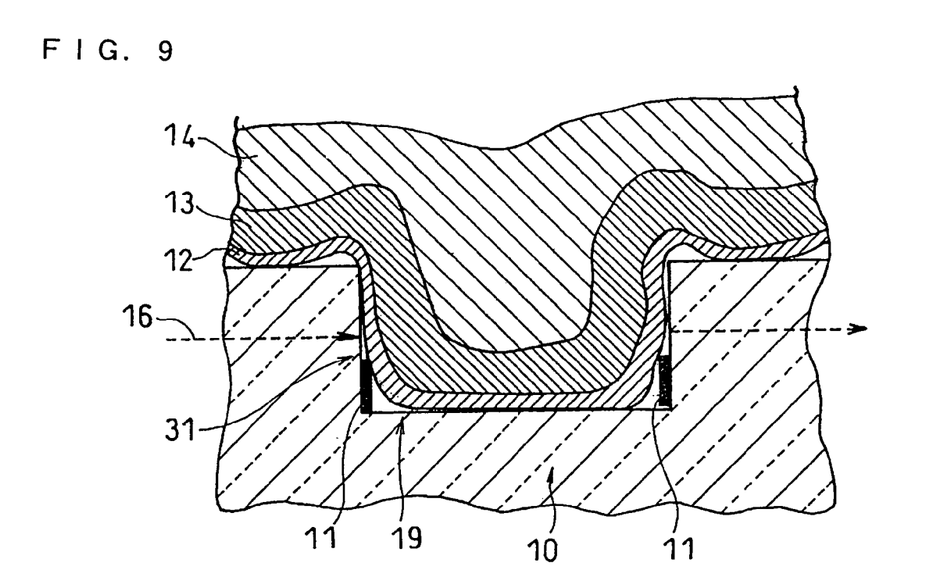
FIG. 9 is a cross sectional view of a part where a groove 10 of an optical apparatus for measuring information of living body and a tissue of living body 20 are making contact in still another embodiment of the present invention.

Although the optical elements 100 in the above embodiments have the groove 10 with substantially a shape of a letter V, as shown in FIG. 1, the groove in this embodiment has, a dent-shape, as shown in FIG. 9, for example. In this case, a light transmittance controlling means 11 can be provided at a side surface 31 of the groove 10 of a dent-shape from a valley part 19.

Based on such structure, the bottom of the valley part of the above groove 10 will not be excessively small in size, and a tissue of living body can easily go into the above valley part. Additionally, even when the tissue of living body is deformed at an edge part of the groove, the degree of contact between the tissue of living body and the groove can be secured sufficiently. Therefore, a body fluid component of a test sample such as a living body can be measured noninvasively with high accuracy, stability and ease, when the optical element of this embodiment is used.

EMBODIMENT 6

Figure 10:
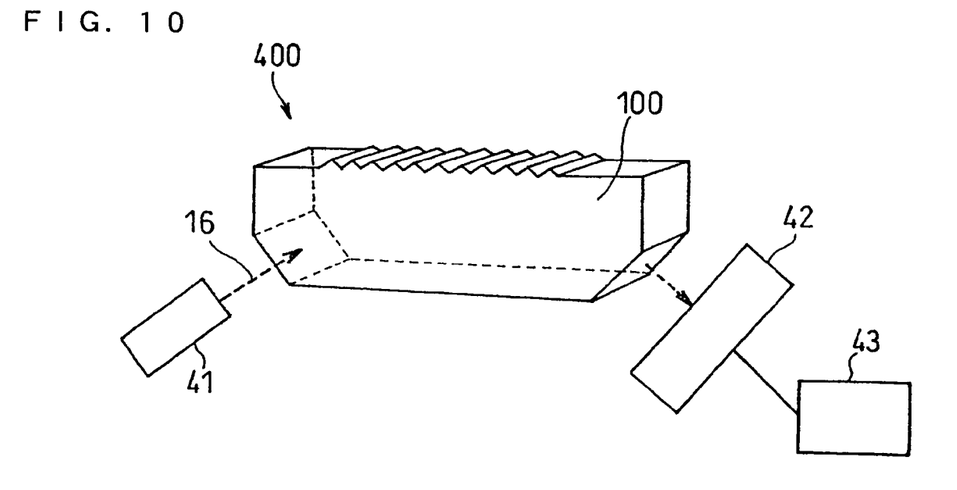
FIG. 10 is a schematic view of an apparatus for measuring information of living body in an embodiment of the present invention.

A schematic view of an apparatus for measuring information of living body of an embodiment of the present invention is shown in FIG. 10. As shown in FIG. 10, the apparatus for measuring information of living body of the present invention is formed from a light source 41, an optical element 100 for measuring information of living body, a photodetector 42, a processor 43, and a spectroscope (not shown) provided in between the light source 41 and the optical element 100 for measuring information of living body.

For the spectroscope, a spectroscope using grating, and Fourier transform spectroscope can be mentioned, for example.

Next, operation of the apparatus for measuring information of living body will be described by using FIG. 10. A light 16 emitted from a light source 41 is applied to the optical element 100 for measuring information of living body. The light 16 applied to the optical element 100 for measuring information of living body is transmitted to the tissue of living body 20 contacting the groove 10 and is scattered, and then emitted from the optical element 100 for measuring information of living body. The light emitted from the optical element 100 for measuring information of living body is detected by the photodetector 42, and the information of living body is processed by the processor 43.

Herein, for the light source 41, a light source which emits a light with absorption wavelength of the component to be a measurement target may be used: for example, LED, a halogen light source, a semiconductor laser, a Globar light source in which SiC is sintered and made into a bar, a $CO_2$ laser, and a tungsten lamp may be mentioned.

When a substance such as glucose having absorption peaks in mid-infrared range of wave number of 1033 $cm^{-1}$, 1080 $cm^{-1}$, and the like, and in near-infrared range of 1 to 2.5 μm, is to be measured with mid-infrared light, it is preferable that the Globar light source is used, in view of the fact that a wide range of wavelength can be covered comparatively, and that the light is emitted well in a range of long wavelength of about 10 μm. Additionally, a halogen light source is preferable when a near-infrared light is to be measured.

As for the material for the optical element 100 for measuring information of living body, a known one in the art can be used according to the wavelength of the light to be used for the measurement. Silicon, germanium, SiC, diamond, ZnSe, ZnS, vitreous silica, calcium fluoride, and KrS can be mentioned, for example.

When a substance such as glucose having absorption peaks in mid-infrared range of wave number of 1033 $cm^{-1}$, 1080 $cm^{-1}$, and the like, and in near-infrared range of 1 to 2.5 μm, is to be measured, it is preferable that the material is silicon or germanium, and that the material has the resistivity of not less than 100 Ωcm with less content of impurity such as boron, phosphorus, and the like.

Further, it is preferable that the material has the resistivity of not less than 1500 Ωcm. In the case of near-infrared range, it is preferable that the material is silicon with the resistivity of not less than 100 Ωcm, and further preferably with the resistivity of not less than 1500 Ωcm. It is also preferable that the material is calcium fluoride, vitreous silica, and the like.

For the photodetector 42, a known detector in the art can be used without particular limitation. For example, in the case of mid-infrared range, MCT detector (mixed crystal of mercury, tellurium, and cadmium), pyroelectric sensor, DTGS detector, thermistor, thermopile, and Golay cell can be mentioned. Additionally, in the case of near-infrared range, PbS detector, InSb detector, PbSe detector, InGaAs detector, and the like can be mentioned.

It is preferable that the processor 43 is a microprocessor, or a computer, although not to be limited thereto.

Next, the structure of the light transmittance controlling means 11 is further described in detail.

For the light transmittance controlling means 11, a known one in the art can be used without particular limitation. For example, the one which is made of a light absorbing material to absorb light can be used, and the one which is made of a light scattering material to scatter the light for decreasing the possibility for the light to go into the photodetector can be used. It also can be a light reflecting material. Also, the light transmittance controlling means 11 can be composed of a single-layered film, and can be composed of a multiple-layered film.

Specifically, it is preferable that the light absorbing material is composed of a single-layered film with an appropriate thickness, or composed of a multiple-layered film, since the light is subjected to multiple interferences in the film to efficiently absorb unnecessary light. As for the material for the light absorbing material (film) in such case, Cu, Cr, Mo, Fe, Ni, amorphous Si, SiC, Ge, $WSi_2$, Ti, TiN, Ta, TiW, Co, SiGe, $TiSi_2$, $CrSi_2$, $MoSi_2$, $FeSi_2$, $NiSi_2$, CrN, $MoN_2$, $SiO_2$, $Al_2O_3$, $TiO_2$, and the like can be mentioned, for example, although not to be limited to thereto. As for the method of forming the light transmittance controlling means 11, a known method in the art can be used without any limitation. For example, chemical vapor deposition, plasma vapor deposition, light chemical vapor deposition, vacuum deposition, liquid-phase epitaxy, sol-gel method, anodic oxidation, oxidation-reduction, laser ablation method, and the like can be mentioned.

Also, when the light transmittance controlling means comprising the light absorbing material is to be provided, impurities such as boron, phosphorous, and the like can be doped in the groove 10 of the optical element 100 for measuring information of living body to absorb a light, by using ion implantation method, for example. In this case, the dope can be conducted directly on a predetermined part of the optical element.

As for the light scattering material, a known one in the art can be used, without any limitation. For example, only in a part in the groove 10 where the light transmittance controlling means 11 is desired to be provided, the surface may be roughened by blasting and the like to scatter the light. Additionally, the light transmittance controlling means 11 may be formed by using both of the light scattering material and the light absorbing material. Concretely, the light absorbing material can be formed by forming the light scattering material by roughening the surface with blasting and then using the means of forming the light absorbing material.

Also, as for the light reflecting material, a known material in the art can be used without any limitation. For example, a thin metal film can be formed with a metal such as aluminum, silver, gold, or copper.

This also applies to the case when the light transmittance controlling means 11' is provided at an entire surface of the optical element except for the light incident surface, the groove, and the light emission surface.

INDUSTRIAL APPLICABILITY

As described above, according to the structure of the optical element of the present invention, the light can be applied reliably to the part where the degree of contact is high, and the light from the part where at least the degree of contact is high can be emitted, even though the bottom of the valley part of the groove became very small in size to prevent the tissue of living body to go into the above valley part, and even though the degree of contact between the tissue of living body and the groove is reduced by a large deformation of the tissue of living body at the peak part in between the grooves.

Therefore, by using the optical element of the present invention, a body fluid component of a test sample such as a living body can be measured noninvasively with high accuracy, stability, and ease: and in the apparatus for measuring information of living body including the above optical element, insufficient degree of contact can be alleviated, and the concentration of the target component in the test sample can be measured stably and easily. Therefore, the present invention is useful in the measurement of body fluid component in medical usage.

The invention claimed is:

1. An optical element for optically measuring information of living body, comprising:
   a light incident surface, a contact surface contacting said living body and having a groove to protrude said living body, and
   a light emission surface,
   wherein said groove comprises:
      a first wall surface,
      a second wall surface, and
      a valley part sandwiched between said first and second wall,
   wherein, said optical element applies light entered into said optical element from said light incident surface to the portion of the living tissue protruded by said groove through said first wall surface, and
   receives light that is absorbed and scattered by the protruded portion of the said living body by said groove through said second wall surface and allows the light to exit said optical element from said light emission surface;
   wherein a light transmittance controlling means is provided at said groove, and said light transmittance controlling means is formed, from a bottom part of said valley part of said groove, to at least a portion of said first wall surface and/or said second wall surface.

2. The optical element for measuring information of living body in accordance with claim 1, wherein said light transmittance controlling means is further provided on a part except for said groove, said light incident surface, and said light emission surface.

3. The optical element for measuring infonnation of living body in accordance with claim 1, wherein said light transmittance controlling means is provided on a peak part of said groove.

4. The optical element for measuring information of living body in accordance with claim 1, wherein said light transmittance controlling means is made of a light absorbing material.

5. The optical element for measuring information of living body in accordance with claim 1, wherein said light transmittance controlling means is made of a light scattering material.

6. The optical element for measuring information of living body in accordance with claim 1, wherein said light transmittance controlling means is made of a light reflecting material.

7. The optical element for measuring information of living body in accordance with any of claims 4 to 6, wherein said light transmittance controlling means is composed of a single-layered film.

8. The optical element for measuring information of living body in accordance with any of claims 4 to 6, wherein said light transmittance controlling means is composed of a multiple-layered film.

9. An apparatus for measuring information of living body, comprising: a light source, the optical element in accordance with claim 1, a photodetector for detecting a light emitted from said optical element, and a processor for processing information obtained from said photodetector.

* * * * *

UNITED STATES PATENT AND TRADEMARK OFFICE
CERTIFICATE OF CORRECTION

PATENT NO. : 7,391,516 B2 Page 1 of 1
APPLICATION NO. : 10/547670
DATED : June 24, 2008
INVENTOR(S) : Masahiko Shioi et al.

It is certified that error appears in the above-identified patent and that said Letters Patent is hereby corrected as shown below:

IN THE CLAIMS:

In Column 12, Line 37 (Claim 3), change "infonnation" to --information--.

Signed and Sealed this

Seventeenth Day of March, 2009

JOHN DOLL
*Acting Director of the United States Patent and Trademark Office*